United States Patent [19]

Wagner et al.

[11] Patent Number: 4,925,476
[45] Date of Patent: May 15, 1990

[54] AZOLE HEMIAMINAL DERIVATIVES AND THEIR USE AS NITRIFICATION INHIBITORS

[75] Inventors: Klaus Wagner, Neustadt; Norbert Rieber, Mannheim; Ernst-Heinrich Pommer, Limburgerhof; Juergen Dressel, Neuhofen, all of Fed. Rep. of Germany

[73] Assignee: BASF Aktiengesellschaft, Ludwigshafen, Fed. Rep. of Germany

[21] Appl. No.: 152,553

[22] Filed: Feb. 5, 1988

[30] Foreign Application Priority Data

Feb. 12, 1987 [DE] Fed. Rep. of Germany ....... 3704359

[51] Int. Cl.$^5$ .................. C05C 11/00; C07D 231/10; C07D 249/08; C07D 233/54
[52] U.S. Cl. .......................................... 71/27; 71/902; 548/374; 548/375; 548/377; 548/378; 548/262; 548/336; 548/337; 548/341; 548/342; 548/517; 548/569; 548/571; 548/573; 548/376; 548/266.6; 548/268.2; 514/383; 514/384; 514/400; 514/406; 514/422; 514/427
[58] Field of Search .............. 548/377, 375, 378, 374, 548/376; 71/902, 7, 27, 92; 514/406

[56] References Cited

U.S. PATENT DOCUMENTS 4,008,249 2/1977 Fischer et al. ....................... 548/375
4,316,040 2/1982 Plath et al. ........................... 548/377
4,673,429 6/1987 Rieber et al. ........................... 71/27

OTHER PUBLICATIONS

Chem. Abstracts, 97: 182306n, No. 21, Nov. 22, 1982, "Heterocyclic Nitro Compounds".
Chem Abstracts, 107:198186j, No. 21, Nov. 23, 1987, "On Triazoles. VI. The Acylation of 5-Amino-1,2 4--Triazoles".

Primary Examiner—Richard L. Raymond
Assistant Examiner—K. L. Konstas
Attorney, Agent, or Firm—Oblon, Spivak, McClelland, Maier & Neustadt

[57] ABSTRACT

Nitrification inhibitors contain azole hemiaminal derivatives of the formula

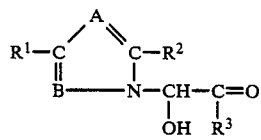

where $R^1$ and $R^2$ are each hydrogen, alkyl, aryl or halogen, $R^3$ is alkyl, cycloalkyl, alkoxy, alkenyl, alkynyl, styryl, aryl, hetaryl or aralkyl, where the aromatic radical may be substituted, or is hydroxyl, A and B are each N or $CR^4$, and $R^4$ is hydrogen, alkyl, aryl or halogen.

7 Claims, No Drawings

AZOLE HEMIAMINAL DERIVATIVES AND THEIR USE AS NITRIFICATION INHIBITORS

The present invention relates to novel azole hemiaminal derivatives and agents containing same for nitrification inhibition of ammonium nitrogen.

It is known that nitrogen suitable for plant nutrition may be present in the soil in the form of ammonium compounds and nitrates.

Ammonium nitrogen is oxidized by bacteria of the genera Nitrosomonas and Nitrobacter via nitrite nitrogen to nitrate nitrogen (nitrification). The extent of this process is essentially dependent on the type of soil, its pH, its moisture content and its biological activity.

Because of the cation-fixing properties of soil (clay, humus), however, nitrate ions are washed out of the soil much more readily than ammonium ions. The result of this is that the nitrogen (nitrate ions) washed out is no longer available for plant nutrition on the one hand and, on the other hand, leads to an undesirable concentration of nitrate in the ground water. Nitrification inhibitors counteract these processes by inhibiting the abovementioned oxidation of the ammonium ions. The biological mechanism of inhibition probably involves inhibition of the growth of the abovementiond bacteria.

Heterocyclic compounds, for example pyridine, pyrimidine, thiazole, thiadiazole, triazole and pyrazole derivatives, ae known nitrification inhibitors. Examples of such compounds are 2-chloro-6-trichloromethylpyridine, 5-ethoxy-3-trichloromethyl-1,2,4-thiadiazole and 3,5-dimethyltetrahydro-1,3,5-thiadiazine-2-thione.

Other known examples are 4-amino-1,2,4-triazole, substituted pyrazoles (U.S. Pat. No. 3,635,690), N-acyl-pyrazoles (German Laid-Open Application DOS 2,745,833, British Patent 1,592,516, East German Patents 131,063 and 133,088, U.S. Pat. No. 3,494,757 and USSR Patent 1,198,049), metalpyrazole complexes (U.S. Pat. No. 4,523,940) and pyrazolium salt-/dicyanodiamine mixtures (East German Patent 222,471). Nitrification-inhibiting 1-hydroxypyrazole derivatives have also been disclosed (DE 3 409 317).

However, the known active ingredients do not meet all requirements in respect to activity, duration of action, cost-effectiveness, safety and performance characteristics, such as water solubility, dispersibility, vapor pressure, etc. Furthermore, they have a very nonspecific action and also attack soil bacteria which are not intended to be damaged.

It is an object of the present invention to provide nitrification inhibitors whose properties in the stated areas are more advantageous than those of the conventional agents of this type.

We have found that this object is achieved by azole hemiaminals of the formula (I)

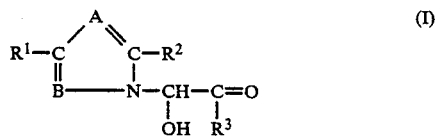

where $R^1$ and $R_2$ independently of one another are each hydrogen, $C_1$–$C_4$-alkyl, unsubstituted or substituted aryl or halogen, $R^3$ is hydroxyl or an open-chain or cyclic $C_1$–$C_{10}$-alkyl or $C_1$–$C_4$-alkoxy, $C_2$–$C_4$-alkenyl, $C_3$- or $C_4$-alkynyl or styryl radical or aryl, hetaryl or aralkyl, where the aromatic radical may be monosubstituted or polysubstituted by halogen, halo-$C_1$–$C_4$-alkyl, halo-$C_1$–$C_4$-alkoxy, $C_1$–$C_4$-alkyl, $C_1$–$C_4$-alkoxy, carboxyl, carboxy-$C_1$–$C_1$-alkyl, cyano, nitro, sulfoxyl or sulfonyl, A and B independently of one another are each N or $CR^4$, and $R_4$ is hydrogen, $C_1$–$C_4$-alkyl, unsubstituted or substituted stituted aryl or halogen.

The novel substances can be prepared by reacting an unsubstituted or substituted azole of the formula (II)

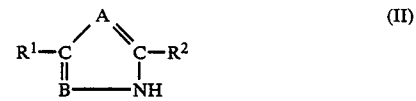

where $R^1$, $R^2$, A and B have the above meanings, or its salts, with a glyoxal, glyoxylic acid or glyoxylate of the formula (III)

where $R^3$ has the above meanings, or its hydrate.

The novel azole hemiaminals of the formula (I) are suitable for inhibiting nitrification. Surprisingly, they have a better and longer-lasting action than the known compounds.

$R^1$ is, for example, $C_1$–$C_4$-alkyl, such as methyl, aryl, such as phenyl, or halogen, such as chlorine or bromine.

$R^2$ is, for example, hydrogen.

$R^3$ is, for example, $C_1$–$C_{10}$-alkyl, such as methyl, ethyl, propyl, isopropyl, butyl, tert-butyl, hexyl or decyl, $C_1$–$C_4$-alkoxy, such as methoxy, ethoxy or butoxy, aryl, such as phenyl, naphthyl or styryl, the thiophene radical, halophenyl, such as chlorophenyl or dichlorophenyl, $C_1$–$C_4$-alkoxyphenyl, such as methoxyphenyl, nitrophenyl or $C_6$–$C_8$-cycloalkyl, such as cyclohexyl.

$R^4$ is, for example, halogen, such as chlorine or bromine, or $C_1$–$C_4$-alkyl, such as methyl.

The novel substances are defined by the general formula (I). In this formula,

A and B are each N or $CR^4$, $R^1$, $R^2$ and $R^4$, independently of one another are each preferably halogen, preferably chlorine or bromine, hydrogen, straight-chain or branched alkyl of 1 to 4 carbon atoms or unsubstituted or substituted phenyl, preferred substituents being halogen and alkyl of 1 to 4 carbon atoms and up to 3 identical or different halogen atoms, and $R^3$ is preferably straight-chain or branched alkyl of 1 to 10 carbon atoms, cyclic alkyl of 3 to 8 carbon atoms, straight-chain or branched $C_2$–$C_4$-alkenyl or $C_3$- or $C_4$-alkynyl, straight-chain or branched $C_1$–$C_4$-alkoxy, hydroxyl or unsubstituted or substituted phenyl whose preferred substituents are halogen, in particular chlorine, alkyl of 1 to 4 carbon atoms, nitro or $C_1$–$C_4$-alkoxy.

Particularly preferred compounds of the formula (I) are those in which A and B independently of one another are each N or $CR^4$, $R^1$, $R^2$ and $R^4$ independently of one another are each chlorine, bromine, methyl, ethyl or phenyl, and $R^3$ is methyl, ethyl, n-propyl, isopropyl, n-butyl, sec-butyl, tert-butyl, isobutyl, cyclopropyl, cyclohexyl, phenyl or styryl.

While the preparation of azole hemiaminals from azoles and simple aldehydes and their use as synthetic building blocks are known (European Patents 51,278 and 8,056 and DE 2 835 158), the substances of the formula (I) are novel.

In general, the novel substances can be obtained by reacting the azole with the glyoxal derivative in stoichiometric amounts. In this procedure, the azole can be used either as the free base or in the form of its salt.

The glyoxal component can likewise be used as the pure substance or in the form of its hydrate. However, it may be advantageous to dehydrate the hydrate before the reaction by azeotropic distillation.

The reactions are generally carried out at from $-20°$ to $100°$ C., in particular from $20°$ to $40°$ C. Suitable solvents are water and organic solvents, such as aliphatic or aromatic hydrocarbons and chlorohydrocarbons, ethers, ketones, amides, nitriles and alcohols.

Where necessary, the reaction can be catalyzed by Brönsted or Lewis acids, for example by acidic ion exchangers.

The novel substances listed in Table 1 were prepared as described in the Examples given. Their structure was determined by the conventional methods.

EXAMPLE 1

3.3 g (29 millimoles) of freshly distilled tert-butylglyoxal (cf. R. C. Fuson, H. Gray and J. J. Gouza, J. Am. Chem. Soc. 61 (1939), 1937) in 50 ml of methylene chloride were initially taken. 3 g (29 millimoles) of 4-chloropyrazole were added, after which the mixture was stirred for 15 hours at room temperature ($20°$ C.), the solvent was evaporated off under reduced pressure and the product was recrystallized from petroleum ether. This procedure gave 5.0 g (80%) of a white substance (compound 03 in Table 1) of melting point $104°$ C.

EXAMPLE 2

1.0 g (8.1 millimoles) of tert-butylglyoxal hemihydrate were refluxed with 50 ml of toluene until water was no longer separated off. Thereafter, 0.8 g (8.1 millimoles) of 4-chloropyrazole are added to the cooled solution, and the mixture was stirred for 5 hours at room temperature. The solvent was stripped off under reduced pressure to give 1.69 g (98%) of product, which could be sublimed at $55°-70°$ C./1 mbar (compound 03 in Table 1, mp. $104°$ C.).

EXAMPLE 3

1.7 g (25 millimoles) of pyrazole were added to 6.0 g (25 millimoles) of a 30% strength by weight aqueous solution of methylglyoxal, and the mixture was stirred for 16 hours at room temperature. Thereafter, it was extracted 3 times with ether, the combined ether phases were washed with saturated NaCl solution and dried over $MgSO_4$, and the solvent was evaporated off under reduced pressure. Distillation of the residue ($70°-80°$ C./1 mbar) gave 2.6 g (74%) of a colorless, viscous substance (compound 19 in Table 1) whose spectroscopic data were in agreement with the expected structure.

EXAMPLE 4

3.85 g (25 millimoles) of phenylglyoxal hydrate were refluxed with 50 ml of toluene until water was no longer separated off. The mixture was cooled, after which 2.05 g (25 millimoles) of 3-methylpyrazole were added and the mixture was stirred for about 10 minutes. 4.5 g (83%) of a precipitated solid substance (compound 22 in Table 1) were then filtered off under suction and recrystallized from ethyl acetate/petroleum ether (mp. $133°$ C.).

EXAMPLE 5

2.0 g (20 millimoles) of ethyl glyoxylate and 2.0 g (20 millimoles) of 4-chloropyrazole in 30 ml of methylene chloride were stirred for 3 days at room temperature. When the starting material was no longer detectable by thin-layer chromatography, the solvent was stripped off under reduced pressure and the product recrystallized. 4.0 g (100%) of a white substance (compound 17 in Table 1) of melting point $100°$ C. were isolated in this manner.

EXAMPLE 6

4.0 g (57 millimoles) of 1,2,4-triazole in 50 ml of acetone were added dropwise at room temperature to 8.1 g (61 millimoles) freshly distilled tert-butylglyoxal in 2.5 ml of benzene. The mixture was stirred for a further 16 hours at room temperature, after which the white precipitate was filtered off under suction, the mother liquor evaporated down and both solid fractions recrystallized together from petroleum ether/ethyl acetate. 9.1 g (86%) of a solid of melting point $130°$ C. (compound 26 in Table 1) were obtained in this manner.

EXAMPLE 7

3.04 g (20 millimoles) of phenylglyoxal hydrate were dissolved in 50 ml of toluene, and the resulting water was removed by azeotropic distillation. The mixture was cooled, after which 2.31 g (20 millimoles) of 5-chloro-4-methylimidazole in 30 ml of methylene chloride were added while cooling with ice. Thereafter, a pinch of ion exchanger (H+) was added, and stirring was carried out for 16 hours at room temperature. The precipitated white product and the solid product obtained after stripping off the solvent under reduced pressure were recrystallized from petroleum ether/ethyl acetate. 4.2 g (84%) of a white substance (compound 29 in Table 1) of melting point $125°$ C. were isolated.

TABLE 1

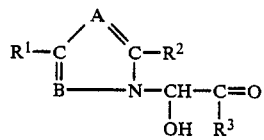

| No. | A | B | $R^1$ | $R^2$ | $R^3$ | mp. [°C.] |
|---|---|---|---|---|---|---|
| 01 | C—Cl | N | H | H | $CH_3$ | 81 |
| 02 | C—Cl | N | H | H | $CH(CH_3)_2$ | 103 |
| 03 | C—Cl | N | H | H | $C(CH_3)_3$ | 104 |

TABLE 1-continued

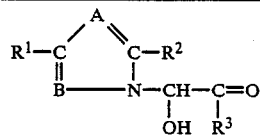

| No. | A | B | R¹ | R² | R³ | mp. [°C.] |
|---|---|---|---|---|---|---|
| 04 | C—Cl | N | H | H | $C_6H_{13}$ | 118 |
| 05 | C—Cl | N | H | H | $C_{10}H_{21}$ (n-decyl-) | |
| 06 | C—Cl | N | H | H | $C_6H_{11}$ (cyclohexyl-) | 124 |
| 07 | C—Cl | N | H | H | $C_6H_5$ (phenyl) | 178 |
| 08 | C—Cl | N | H | H | 2-$C_{10}H_7$ (2-naphthyl-) | 200 |
| 09 | C—Cl | N | H | H | (p-Cl)—$C_6H_4$ | 150 |
| 10 | C—Cl | N | H | H | (o-$OCH_3$)—$C_6H_4$ | 74 |
| 11 | C—Cl | N | H | H | (p-$OCH_3$)—$C_6H_4$ | 135 |
| 12 | C—Cl | N | H | H | (p-$NO_2$)—$C_6H_4$ | 110 |
| 13 | C—Cl | N | H | H | (o,p-$Cl_2$)—$C_6H_3$ | 138 |
| 14 | C—Cl | N | H | H | CH=CH—$C_6H_5$ (styryl-) | 155 |
| 15 | C—Cl | N | H | H | 2-$C_4H_3$S (2-thio-phenyl) | 171 |
| 16 | C—Cl | N | H | H | OH | 166 |
| 17 | C—Cl | N | H | H | $OC_2H_5$ | 100 |
| 18 | C—Cl | N | H | H | $OC_4H_9$ | 67 |
| 19 | C—H | N | H | H | $CH_3$ | oil |
| 20 | C—H | N | H | H | $C_6H_5$ | 140 |
| 21 | C—H | N | $CH_3$ | H | $CH_3$ | oil |
| 22 | C—H | N | $CH_3$ | H | $C_6H_5$ | 133 |
| 23 | C—Br | N | H | H | $C_6H_5$ | 172 |
| 24a | C—Br | N | Br | H | $C_6H_5$ | 74 |
| 24b | C—Br | N | H | Br | $C_6H_5$ | |
| 25 | C—I | N | H | H | $C_6H_5$ | 164 |
| 26 | N | N | H | H | $C(CH_3)_3$ | 130 |
| 27 | N | N | H | H | $C_6H_5$ | 146 |
| 28 | N | C—H | H | H | $C_6H_5$ | 108 |
| 29 | N | C—Cl | $CH_3$ | H | $C_6H_5$ | 125 |
| 30 | N | C—Cl | Cl | H | $C_6H_5$ | 113 |

An example of a carrier is water, an organic liquid or a conventional inert solid carrier, for example clay, powdered quartz, talc or chalk.

The action of the novel compounds can be tested, for example, in the manner described below.

220 mg of ammonium sulfate were added to 200 g of an unsterilized loamy sand which was taken from the field and whose moisture content was brought to 50% of its water capacity, and were mixed thoroughly with the soil. Thereafter, the active ingredients, dissolved in 0.2 ml of acetone, were added, in each case in an amount of 1 ppm, based on moist sand. The soil samples were mixed carefully and thoroughly, the acetone was evaporated in 1 liter glass containers covered with aluminum foil to prevent water losses, and the soil samples were then incubated, together with the controls without the addition of active ingredient, for from 28 to 42 days at 21° C. (after this period, a soil sample with normal soil conditions generally no longer contains detectable amounts of ammonium nitrogen).

2.5 g of each of the soil samples were then introduced into 100 ml conical flasks, and 22.5 ml of a 0.1N potassium sulfate solution were added. After shaking for 30 minutes, the samples were filtered and 2.5 ml of each of the soil extracts were mixed with 1,625 ml of distilled water. To detect the ammonium ions still present in the soil extract, 1.25 ml of Nessler's reagent were then added and the mixture shaken thoroughly. The color changes were then measured photometrically at a wavelength of 420 mm. The amounts of ammonium sulfate still present in the soil samples were determined from standard curves based on measurement of solutions having known ammonium sulfate contents. The percentage inhibition of nitrification in the treated soil samples was calculated with reference to the untreated soil samples (only ammonium sulfate added), using the following formula:

$$\ldots \% \text{ inhibition of nitrification} = \frac{a - b}{a} \times 100$$

a = nitrification rate of ammonium sulfate in the absence of a nitrification inhibitor (taken as 100% or 1.0)

b = nitrification rate of ammonium sulfate in the presence of a nitrification inhibitor

| Active ingredient no. | % inhibition of nitrification 4 and 6 weeks after addition of 1 ppm of active ingredient to the soil | |
|---|---|---|
| | 4 | 6 |
| 2 | 100 | 95 |
| 3 | 100 | 92 |
| 6 | 100 | 97 |
| 17 | 100 | 89 |
| 18 | 100 | 97 |
| 23 | 100 | 89 |

We claim:

1. An azole hemiaminal derivative of the formula:

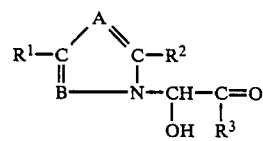

where $R^1$ and $R^2$ independently of one another are each hydrogen, $C_1$-$C_4$-alkyl, unsubstituted or substituted aryl or halogen, wherein the substituents on the aryl are selected from the group consisting of halogen and $C_1$-$C_4$ alkyl, $R^3$ is hydroxyl or an open-chain or cyclic $C_1$-$C_{10}$-alkyl or $C_1$-$C_4$-alkoxy, $C_2$-$C_4$-alkenyl, $C_3$- or $C_4$-alkynyl or styryl radical or phenyl, naphthyl, or thiophenyl or aralkyl, where the aromatic radical of each aromatic radical containing group may be monosubstituted or polysubstituted by halogen, halo-$C_1$-$C_4$-alkyl, halo-$C_1$-$C_4$-alkoxy, $C_1$-$C_4$-alkyl, $C_1$-$C_4$-alkoxy, carboxyl, carboxy-$C_1$-$C_4$-alkyl, cyano, nitro, sulfoxyl or sulfonyl, A is $CR^4$ and B is N, and $R^4$ is hydrogen, $C_1$-$C_4$-alkyl, unsubstituted or substituted aryl or halogen wherein the substituents on the aryl are selected from the group consisting of halogen and $C_1$-$C_4$ alkyl.

2. A nitrification inhibitor comprising: an azole hemiaminal derivative of the formula (I)

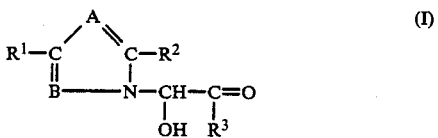

where $R^1$ and $R^2$ independently of one another are each hydrogen, $C_1$-$C_4$-alkyl, unsubstituted or substituted aryl or halogen, wherein the substituents on the aryl are selected from the group consisting of halogen and $C_1$-$C_4$ alkyl, $R^3$ is hydroxyl or an open-chain or cyclic $C_1$-$C_{10}$-alkyl or $C_1$-$C_4$-alkoxy, $C_2$-$C_4$-alkenyl, $C_3$- or $C_4$-alkynyl or styryl radical or phenyl, naphthyl, or thiophenyl or aralkyl, where the aromatic radical of each aromatic radical containing group may be monosubstituted or polysubstituted by halogen, halo-$C_1$-$C_4$-alkyl, halo-$C_1$-$C_4$-alkoxy, $C_1$-$C_4$-alkyl, $C_1$-$C_4$-alkoxy, carboxyl, carboxy-$C_1$-$C_4$-alkyl, cyano, nitro, sulfoxyl or sulfonyl, A is $CR^4$ and B is N, and $R^4$ is hydrogen, $C_1$-$C_4$-alkyl, unsubstitured or substituted aryl or halogen wherein the substituents on the aryl are selected from the group consisting of halogen and $C_1$-$C_4$ alkyl, in combination with a carrier.

3. A process for inhibiting nitrification in the soil, wherein an azole hemiaminal derivative of the formula (I)

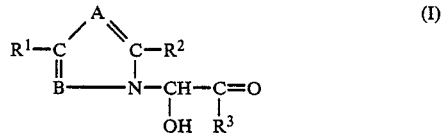

where $R^1$ and $R^2$ independently of one another are each hydrogen, $C_1$-$C_4$-alkyl, unsubstituted or substituted aryl or halogen, wherein the substituents on the aryl are selected from the group consisting of halogen and $C_1$-$C_4$ alkyl, $R^3$ is hydroxyl or an open-chain or cyclic $C_1$-$C_{10}$-alkyl or $C_1$-$C_4$-alkoxy, $C_2$-$C_4$-alkenyl, $C_3$- or $C_4$-alkynyl or styryl radical or phenyl napthyl orthiophenyl or aralkyl, where the aromatic radical of each aromatic containing group may be monosubstituted or polysubstituted by halogen, halo-$C_1$-$C_4$-alkyl, halo-$C_1$-$C_4$-alkoxy, $C_1$-$C_4$-alkyl, $C_1$-$C_4$-alkoxy, carboxyl, carboxy-$C_1$-$C_4$-alkyl, cyano, nitro, sulfoxyl or sulfonyl, A is $CR^4$ and B is N, and $R^4$ is hydrogen, $C_1$-$C_4$-alkyl, unsubstituted or substituted aryl or halogen, wherein the substituents on the aryl are selected from the group consisting of halogen and $C_1$-$C_4$ alkyl, is applied to the soil in an amount sufficient for inhibition.

4. A compound as claimed in claim 1, wherein A is C-Cl, B is N, $R^1$ and $R^2$ are each H and $R^3$ is $C_1$-$C_4$-alkyl or phenyl.

5. A compound as claimed in claim 1, wherein A is C-Cl, B is N, $R^1$ and $R^2$ are each H and $R^3$ is $C(CH_3)_3$.

6. The azole hemiaminal derivative of claim 1, wherein A is C-Br, B is nitrogen, $R^1$ and $R^2$ are each hydrogen and $R^3$ is phenyl.

7. The compound as claimed in claim 1, wherein A is $CR^4$ and B is N $R^1$, $R^2$ and $R^4$ each independently is chlorine, bromine, methyl, ethyl or phenyl and $R^3$ is methyl, ethyl, n-propyl, isopropyl, n-butyl, sec-butyl, t-butyl, isobutyl, cyclopropyl, cyclohexyl, phenyl or styryl.

* * * * *